(12) United States Patent
Koumoto et al.

(10) Patent No.: US 8,752,421 B2
(45) Date of Patent: Jun. 17, 2014

(54) FLAW DETECTION TESTING DEVICE FOR HUB UNIT

(75) Inventors: Masashi Koumoto, Yao (JP); Masahiro Ueno, Kashiba (JP)

(73) Assignee: JTEKT Corporation, Osaka-Shi (JP)

( * ) Notice: Subject to any disclaimer, the term of this patent is extended or adjusted under 35 U.S.C. 154(b) by 221 days.

(21) Appl. No.: 13/345,988

(22) Filed: Jan. 9, 2012

(65) Prior Publication Data

US 2012/0180559 A1 Jul. 19, 2012

(30) Foreign Application Priority Data

Jan. 19, 2011 (JP) ................................. 2011-008503

(51) Int. Cl.
*G01M 17/10* (2006.01)

(52) U.S. Cl.
USPC ..................................................... 73/115.07

(58) Field of Classification Search
USPC ................ 73/115.01, 115.07, 115.08, 117.01
See application file for complete search history.

(56) References Cited

U.S. PATENT DOCUMENTS

| | | | | |
|---|---|---|---|---|
| 4,499,759 A | * | 2/1985 | Hull | 73/146 |
| 5,148,104 A | * | 9/1992 | Ishikawa | 324/173 |
| 5,576,496 A | * | 11/1996 | Carlini et al. | 73/460 |
| 5,604,317 A | * | 2/1997 | Jachmann et al. | 73/862.191 |
| 5,894,094 A | * | 4/1999 | Kuchler et al. | 73/862.044 |
| 6,494,471 B2 | * | 12/2002 | Lukac | 280/93.5 |
| 8,056,406 B2 | * | 11/2011 | Goto et al. | 73/117.01 |
| 2002/0100321 A1 | * | 8/2002 | Douglas et al. | 73/461 |
| 2007/0089306 A1 | * | 4/2007 | Hohlrieder et al. | 33/203.18 |
| 2007/0261499 A1 | * | 11/2007 | Hamilton | 73/798 |
| 2010/0038958 A1 | | 2/2010 | Tsuzaki et al. | |

FOREIGN PATENT DOCUMENTS

| | | |
|---|---|---|
| JP | A-2007-276780 | 10/2007 |
| JP | A-2008-174178 | 7/2008 |

OTHER PUBLICATIONS

Feb. 28, 2014 Search Report issued in European Patent Application No. 12151244.6.

* cited by examiner

*Primary Examiner* — Eric S McCall
(74) *Attorney, Agent, or Firm* — Oliff PLC

(57) ABSTRACT

A flaw detection testing device that carries out a flaw detection test on an outer peripheral surface of a clinched portion used to fix an inner ring member of a hub unit to a hub spindle includes: a flaw detection sensor; a clearance setting member that contacts the outer peripheral surface of the clinched portion to set a clearance between the flaw detection sensor and the outer peripheral surface of the clinched portion at a predetermined value; a fixing device that fixes a position of the flaw detection sensor with the clearance between the flaw detection sensor and the outer peripheral surface kept at the predetermined value; and an actuating device that moves the clearance setting member in such a direction that the clearance setting member is separated from the outer peripheral surface of the clinched portion with the position of the flaw detection sensor fixed by the fixing device.

12 Claims, 6 Drawing Sheets

FLAW DETECTION TESTING DEVICE FOR HUB UNIT

The disclosure of Japanese Patent Application No. 2011-008503 filed on Jan. 19, 2011 including the specification, drawings and abstract, is incorporated herein by reference in its entirety.

BACKGROUND OF THE INVENTION

1. Field of the Invention

The invention relates to a flaw detection testing device for a hub unit that supports a wheel of an automobile.

2. Description of Related Art

There is known a hub unit that includes a hub wheel, an inner ring member and rolling elements and that rotatably supports a wheel of an automobile (for example, see Japanese Patent Application Publication No. 2007-276780 (JP-A-2007-276780)). The hub wheel has a hub spindle. The inner ring member is fixed to the vehicle body-side end portion of the hub spindle. The rolling elements are rollably provided between an inner ring raceway and an outer ring raceway. The inner ring raceway is formed on the outer periphery of the hub spindle and inner ring member. The outer ring raceway is formed on the inner periphery of an outer ring.

A small-diameter portion is formed at the vehicle body-side end portion of the hub spindle via a step in the hub unit. The inner ring member is fitted around the outer peripheral surface of the small-diameter portion. The inner ring member is fixed to the hub spindle by clinching, by plastically deforming the distal end of the small-diameter portion, protruding from the inner ring member, radially outward.

The rotational driving force of a drive shaft is transmitted to the hub unit via a constant velocity joint. There is known the following manner of transmitting the rotational driving force. Spline teeth are formed at the distal end portion of the small-diameter portion of the hub spindle, that is, the axial end surface of the clinched portion, spline teeth are also formed on the axial end surface of the outer ring of the constant velocity joint, facing the axial end surface of the clinched portion, and both the spline teeth are in mesh with each other (for example, see Japanese Patent Application Publication No. 2008-174178 (JP-A-2008-174178)).

The above-described hub unit is subjected to flaw detection test to check whether a flaw or a crack has occurred in the clinched portion. This test is carried out, for example, in the following manner. The hub unit is rotated in a state where an eddy current sensor is brought close to the clinched portion with a set clearance left, and then a change in the value detected by the eddy current sensor is acquired. In the case of the hub unit described in JP-A-2007-276780, a flaw detection sensor is brought close to the axial end surface of the clinched portion to thereby make it possible to carry out a flaw detection test. On the other hand, in the case of the hub unit described in JP-A-2008-174178, the spline teeth are formed on the axial end surface of the clinched portion, and a flaw, or the like, tends to occur near the intersection between the spline teeth and the outer peripheral surface of the clinched portion. Therefore, it is necessary to carry out the test with the flaw detection sensor brought close to the outer peripheral surface. However, the shape of the outer peripheral surface of the clinched portion is not restrained when the clinched portion is plastically deformed. Therefore, the outside diameter size tends to vary from product to product, and it is necessary to adjust the clearance between the outer peripheral surface of the clinched portion and the eddy current sensor for each product in order to carry out an accurate flaw detection test.

SUMMARY OF THE INVENTION

It is an object of the invention to provide a flaw detection testing device for a hub unit, that is able to carry out an accurate flaw detection test even if the clearance between the outer peripheral surface of a clinched portion and a flaw detection sensor is not adjusted for each product.

An aspect of the invention relates to a flaw detection testing device that carries out a flaw detection test on an outer peripheral surface of a clinched portion used to fix an inner ring member of a hub unit to a hub spindle. The flow detection testing device includes: a flaw detection sensor; a clearance setting member that contacts the outer peripheral surface of the clinched portion to set a clearance between the flaw detection sensor and the outer peripheral surface of the clinched portion at a predetermined value; and a fixing device that fixes a position of the flaw detection sensor with the clearance between the flaw detection sensor and the outer peripheral surface of the clinched portion kept at the predetermined value.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

Figure 6:
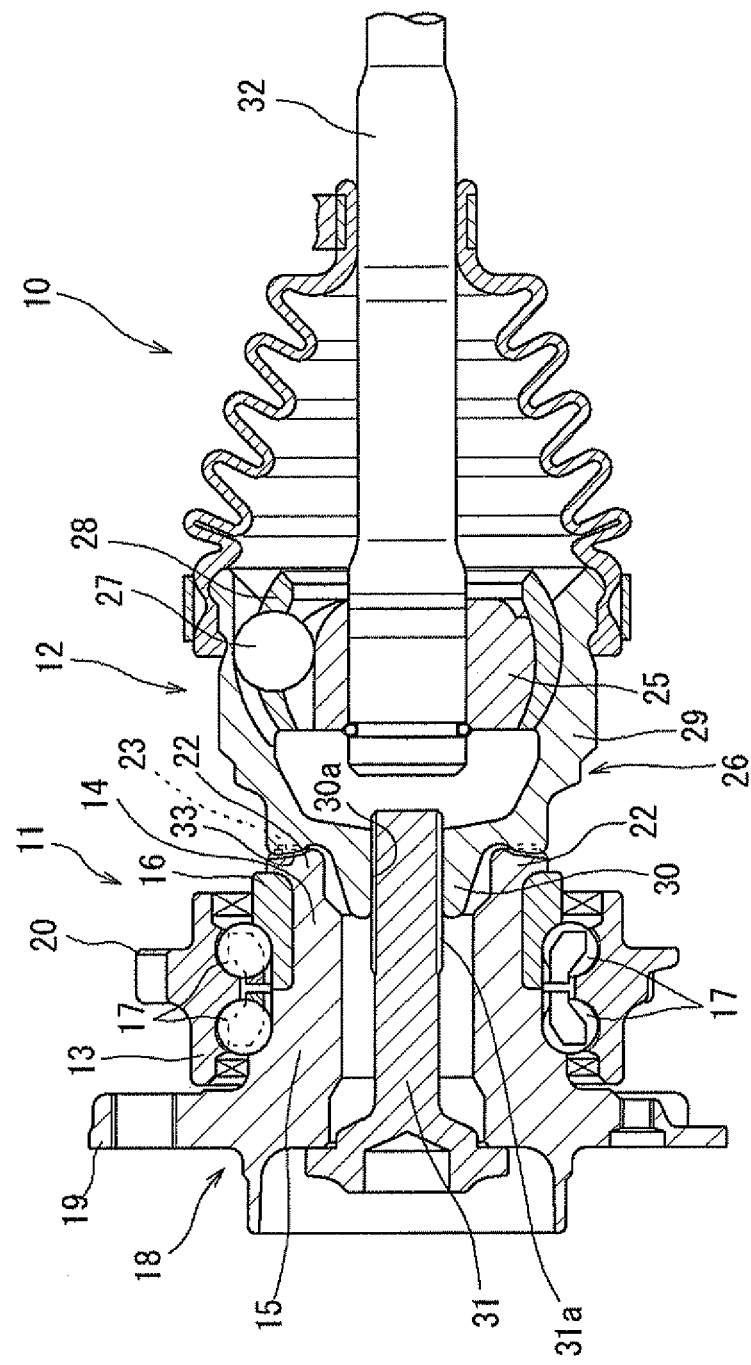
FIG. 6 is a sectional view of a wheel supporting device that includes a hub unit.

Hereinafter, an embodiment of the invention will be described with reference to the accompanying drawings. First, a hub unit 11 that is a measurement target subjected to a test carried out by a flaw detection testing device according to the invention will be described. The test is carried out in order to check whether a flaw or a crack has occurred in the hub unit 11. FIG. 6 is a sectional view of a wheel supporting device 10 that includes the hub unit 11. The wheel supporting device 10 includes the hub unit 11 and a constant velocity joint 12. The hub unit 11 has an outer ring 13, a hub wheel 18 and a plurality of rolling elements 17. The outer ring 13 has a pair of outer ring raceways that are arranged next to each other in the axial direction. The hub wheel 18 has a hub spindle 15. The hub spindle 15 is arranged radially inward of the outer ring 13. The hub spindle 15 has an inner ring raceway that faces one of the outer ring raceways. The hub spindle 15 has a small-diameter portion 14 at its one axial end portion (vehicle body-side end portion). The rolling elements 17 are provided in two rows between the pair of outer ring raceways and the two inner ring raceways.

A flange portion 19 that radially protrudes is integrally formed at a wheel-side end portion (left side in FIG. 6) of the hub spindle 15. Hub bolts (not shown) for mounting a brake disc and a wheel are fitted to the flange portion 19. A mounting flange 20 is integrally formed at the outer periphery of the outer ring 13. The mounting flange 20 is connected to a vehicle body-side knuckle with bolts.

The inner ring member 16 is fitted around the outer peripheral surface of the small-diameter portion 14 of the hub spindle 15, and is fixed to the hub spindle 15 by clinching, by plastically deforming the distal end portion of the small-diameter portion 14 radially outward. Then, multiple spline teeth 23 that extend in a radial fashion are formed on the axial end surface of the distal end portion (hereinafter, also referred to as "clinched portion") of the plastically deformed small-diameter portion 14.

The constant velocity joint 12 includes an inner ring 25, an outer ring 26, a plurality of balls 27 and a cage 28. The inner ring 25 is coupled to one end of a drive shaft 32. The outer ring 26 is arranged on the radially outer side of the inner ring 25. The balls 27 are arranged between the inner ring 25 and the outer ring 26. The cage 28 retains the balls 27. The outer ring 26 has a bowl-shaped outer ring cylindrical portion 29, and an outer ring shaft portion 30. The outer ring shaft portion 30 protrudes from the center portion of the end surface of the outer ring cylindrical portion 29. The outer ring shaft portion 30 has an internal thread 30a formed along its axial direction. An external thread 31a formed on a cap bolt 31 is screwed to the internal thread 30a to connect the hub unit 11 to the constant velocity joint 12.

Spline teeth 33 are formed on the end surface of the outer ring cylindrical portion 29, facing the end surface of the clinched portion 22 of the hub spindle 15, and the spline teeth 23 of the clinched portion 22 are in mesh with the spline teeth 33 of the outer ring cylindrical portion 29 such that torque is transmittable. Thus, the rotational power of the drive shaft 32 is transmitted to the hub unit 11 via the constant velocity joint 12.

As described above, the hub unit 11 has the clinched portion 22 that is used to fix the inner ring member 16 to the hub spindle 15. The clinched portion 22 is subjected to flaw detection test in order to check whether a crack or a flaw has occurred in the clinched portion 22. In the hub unit 11 in which the spline teeth 23 are formed on the axial end surface of the clinched portion 22 as in the case of the present embodiment, a crack, or the like, tends to easily occur on the outer peripheral surface of the clinched portion 22. Therefore, the outer peripheral surface is required to be subjected to flaw detection test. However, the diameter of the outer peripheral surface of the clinched portion 22 tends to vary from product to product, so work for setting a constant clearance between the outer peripheral surface and a flaw detection sensor is complicated.

The flaw detection testing device according to the present embodiment is configured to be able to easily set the position of the flaw detection sensor in response to such variations in the diameter of the outer peripheral surface of the clinched portion 22. Hereinafter, the details of the flaw detection testing device will be described.

Figure 1:
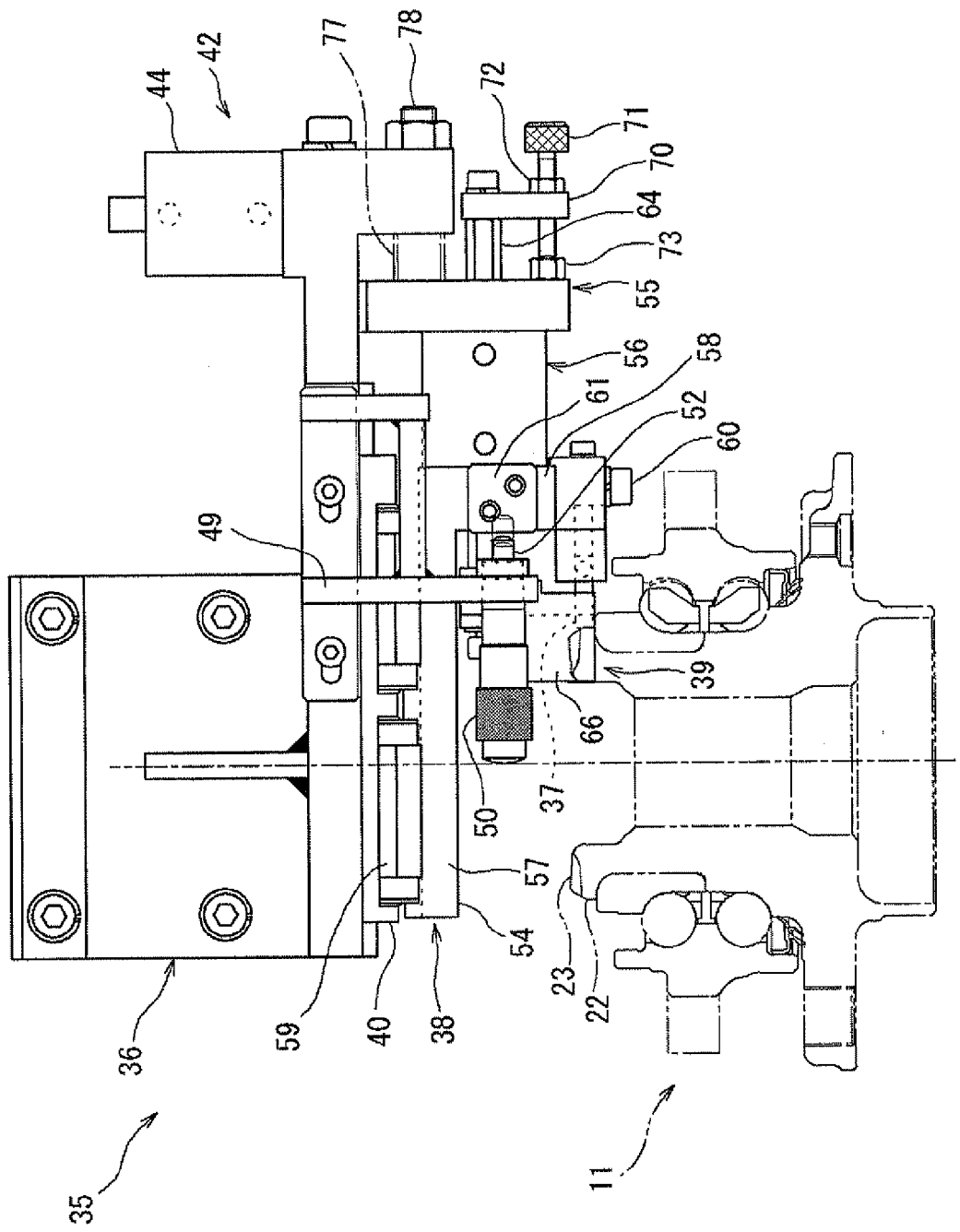
FIG. 1 is a side view of a flaw detection testing device according to an embodiment of the invention.
Figure 2:
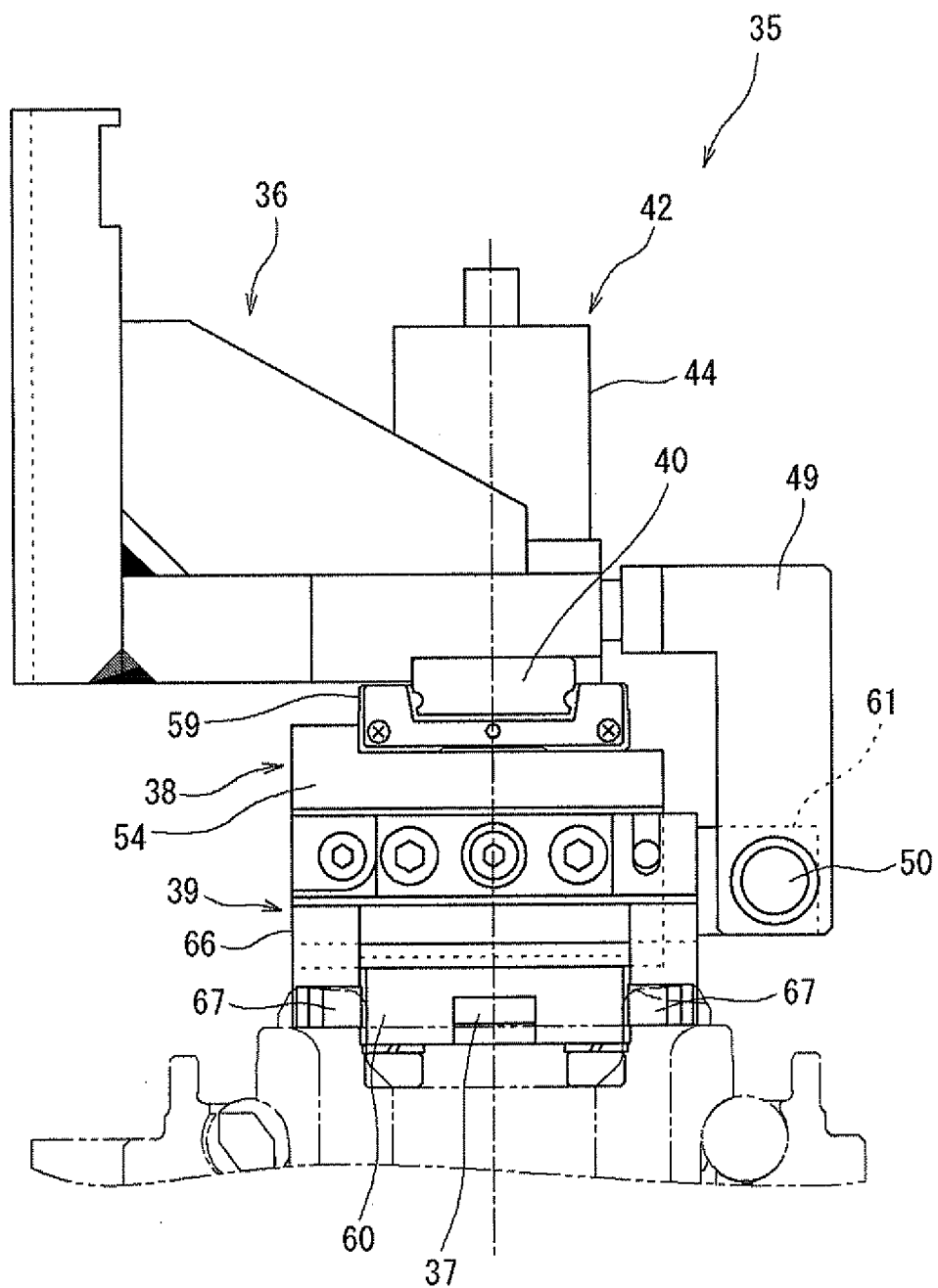
FIG. 2 is a front view of the flaw detection testing device according to the embodiment of the invention.
Figure 3:
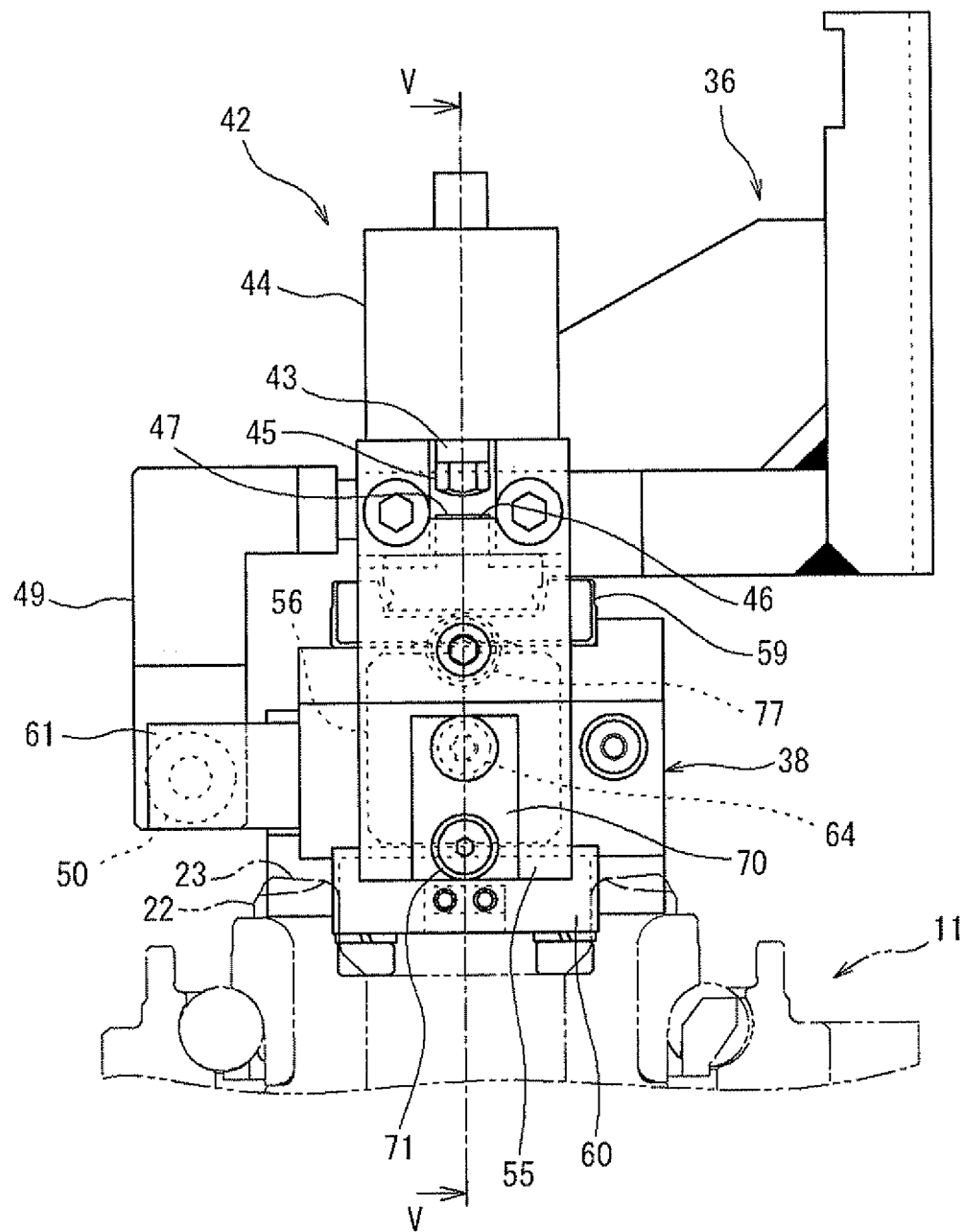
FIG. 3 is a back view of the flaw detection testing device according to the embodiment of the invention.
Figure 4:
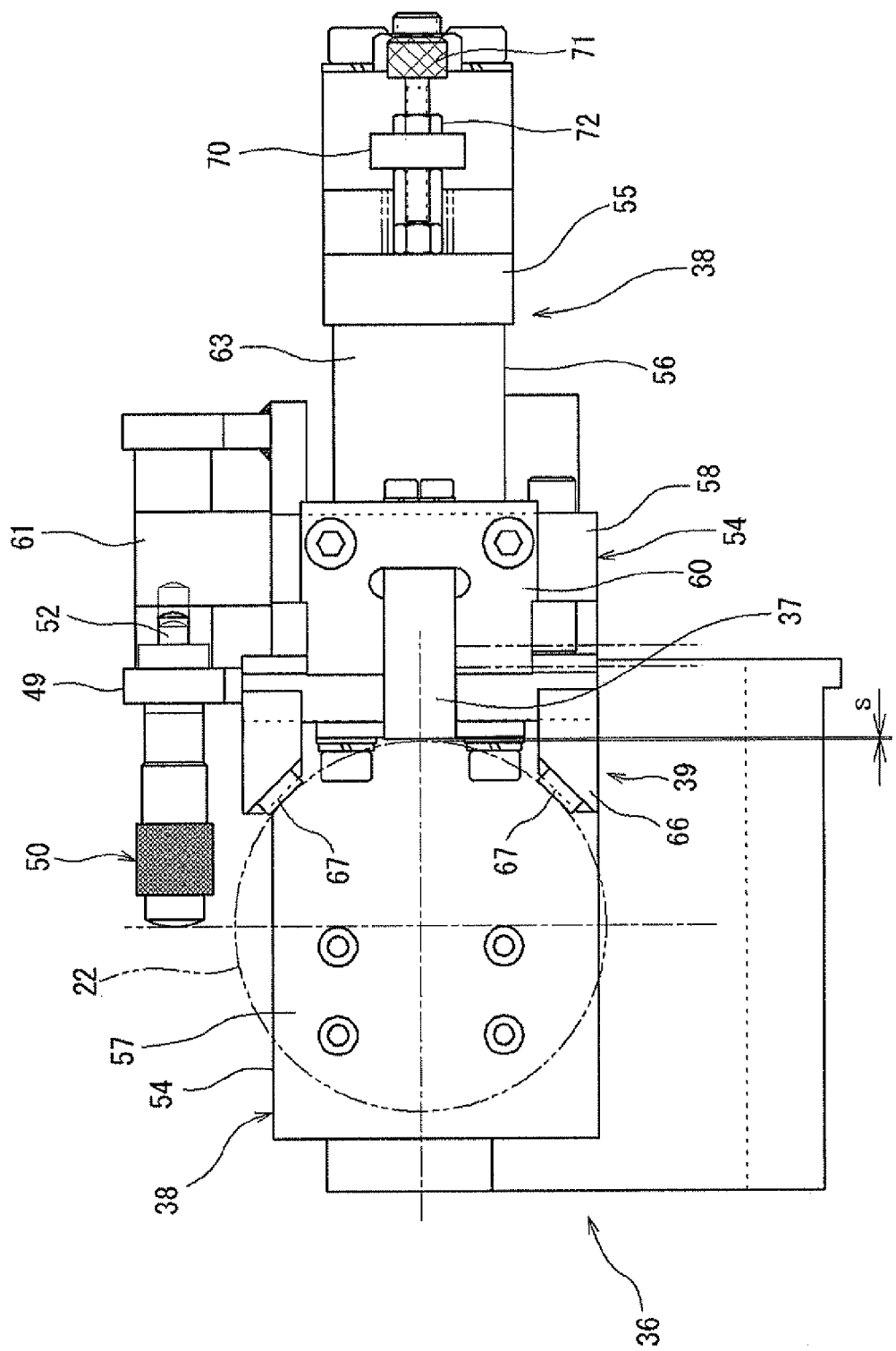
FIG. 4 is a bottom view of the flaw detection testing device according to the embodiment of the invention.
Figure 5:
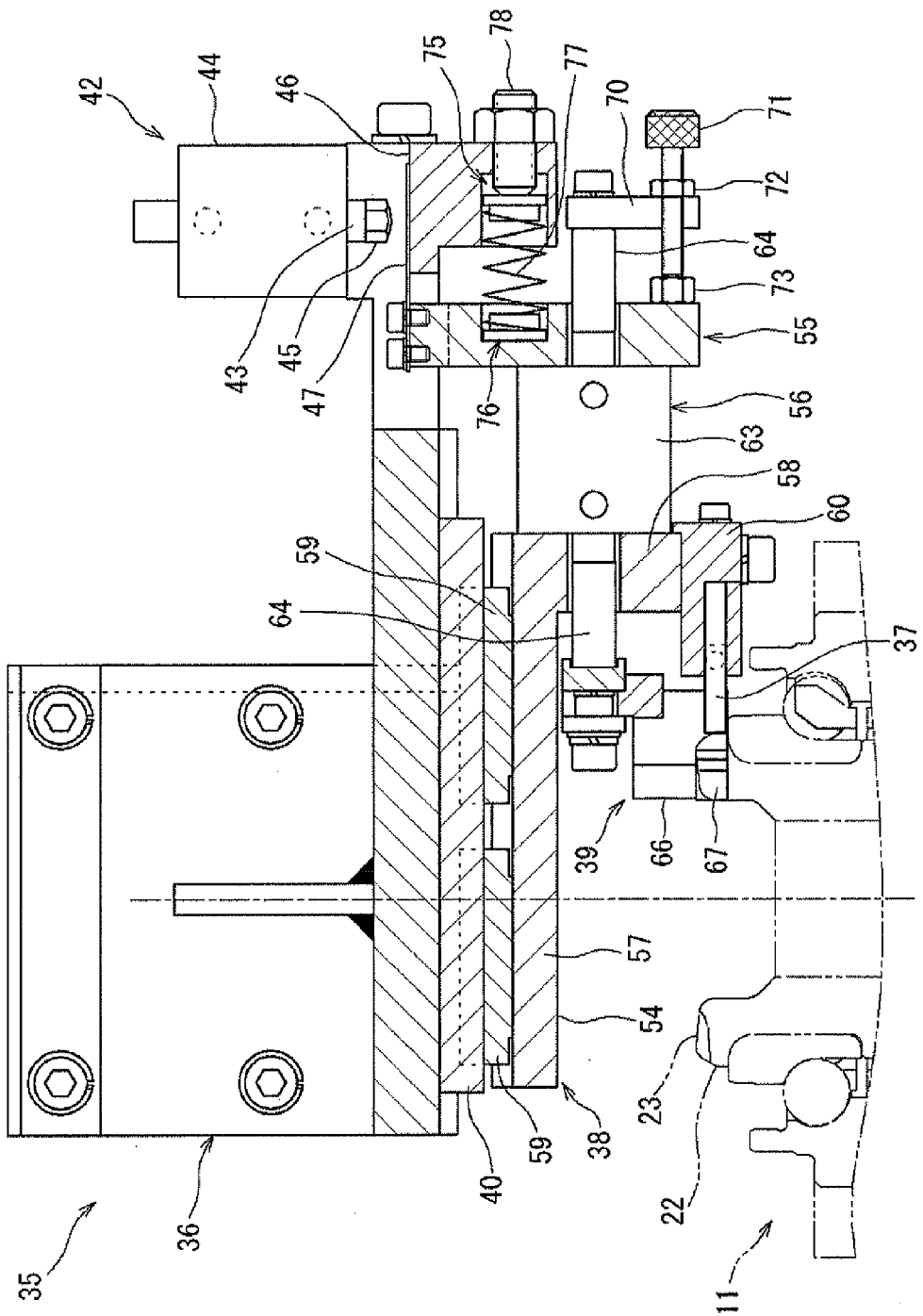
FIG. 5 is a sectional view taken along the line V-V in FIG. 3.

FIG. 1 is a side view of the flaw detection testing device according to the present embodiment. FIG. 2 is a front view of the flaw detection testing device. FIG. 3 is a back view of the flaw detection testing device. FIG. 4 is a bottom view of the flaw detection testing device. FIG. 5 is a sectional view taken along the line V-V in FIG. 3. Note that, in the following description, the right-left direction in FIG. 1 is a front-rear direction, and the direction perpendicular to the sheet on which FIG. 1 is drawn is a lateral direction. The flaw detection testing device 35 is mainly formed of a device body portion 36, a sensor supporting portion 38 and a positioning portion 39. The sensor supporting portion 38 is fitted to the device body portion 36, and supports an eddy current sensor 37 that serves as a flaw detection sensor. The positioning portion 39 positions the eddy current sensor 37 with respect to the clinched portion 22 of the hub unit 11.

As shown in FIG. 1, the device body portion 36 is movable in the up-down direction and the front-rear direction (right-left direction in FIG. 1) by an actuating device (not shown). A rail 40 extending in the front-rear direction is provided at the lower portion of the device body portion 36. The sensor supporting portion 38 is movable in the front-rear direction with respect to the rail 40.

A fixing mechanism (fixing device) 42 is provided at the rear end portion of the device body portion 36. The fixing mechanism 42 restricts movement of the sensor supporting portion 38 in the front-rear direction to fix the sensor supporting portion 38. As shown in FIG. 3 and FIG. 5, the fixing mechanism 42 has a first cylinder 44 and a stopper member 45. The first cylinder 44 has a rod 43 that moves in the up-down direction. The stopper member 45 is fitted to the distal end of the rod 43. The first cylinder 44 is actuated by fluid pressure, such as air pressure and hydraulic pressure. In addition, the device body portion 36 is provided with a stopper receiving portion 46 that is arranged below the stopper member 45 so as to face the stopper member 45. Then, a fixing plate 47 provided at the sensor supporting portion 38 is placed on the stopper receiving portion 46. When the stopper member 45 is moved downward to hold (clamp) the fixing plate 47 between the stopper member 45 and the stopper receiving portion 46, movement of the sensor supporting portion 38 in the front-rear direction is restricted.

As shown in FIG. 1 and FIG. 2, a micrometer (measure) 50 is mounted at one side portion of the device body portion 36 in the right-left direction via a mounting bracket 49. The micrometer 50 incorporates a screw mechanism, and is configured to measure a minute size in the following manner. An adjustment knob is rotated to extend or contract a gauge head 52, and then the rotation amount of the adjustment knob is converted into the extension/contraction amount of the gauge head 52. The micrometer 50 according to the present embodiment is mounted on the device body portion 36 such that the gauge head 52 extends or contracts in the front-rear direction.

As shown in FIG. 5, the sensor supporting portion 38 has a front member 54, a rear member 55 and a second cylinder 56 that connects these members to each other.

The front member 54 is formed of a main portion 57 that extends in the front-rear direction, and a secondary portion 58 that extends downward from the rear end portion of the main portion 57. The front member 54 has a generally inverted-L shape in side view. A guide shoe 59 is provided on the upper surface of the main portion 57. The guide shoe 59 is fitted to the rail 40 so as to be movable in the front-rear direction. The eddy current sensor 37 is attached to the lower portion of the secondary portion 58 via a bracket 60 so as to protrude forward. In addition, as shown in FIG. 1 and FIG. 4, a retaining member 61 is fixed at one side portion of the secondary portion 58 in the right-left direction. The distal end of the gauge head 52 of the micrometer 50 contacts the retaining member 61.

As shown in FIG. 5, the distal end surface of a cylinder body 63 of the second cylinder 56 is connected to the rear end surface of the secondary portion 58 of the front member 54. The second cylinder 56 is actuated by fluid pressure, such as air pressure and hydraulic pressure. The second cylinder 56 has the cylinder body 63 and a rod 64 that extends through the cylinder body 63 in the front-rear direction, and moves in the front-rear direction. The front portion of the rod 64 extends through the secondary portion 58 in the front-rear direction.

A clearance setting member 66 is fixed to the distal end portion of the rod 64 of the second cylinder 56. The clearance setting member 66 constitutes the positioning portion 39. As shown in FIG. 4, the clearance setting member 66 includes two contact portions 67 that contact the outer peripheral surface of the clinched portion 22 of the hub unit 11. The two contact portions 67 are arranged at an interval of about 90 degrees (angle smaller than 180 degrees) about the axis of the hub unit 11. Then, the eddy current sensor 37 is arranged at substantially the center between the two contact portions 67. The rod 64 of the second cylinder 56 is provided with the clearance setting member 66, while the eddy current sensor 37 is fitted to the secondary portion 58 of the front member 54. Therefore, the clearance setting member 66 and the eddy current sensor 37 are movable relative to each other in the front-rear direction as the rod 64 moves in the front-rear direction. In the present embodiment, the two contact portions 67 are brought into contact with the outer peripheral surface of the clinched portion 22 to thereby set the clearance s between the outer peripheral surface of the clinched portion 22 and the distal end surface of the eddy current sensor 37 at a predetermined value.

As shown in FIG. 4 and FIG. 5, the rear member 55 of the sensor supporting portion 38 is fitted to the rear end surface of the second cylinder 56. The rear portion of the rod 64 of the second cylinder 56 extends through the rear member 55. The above-described fixing plate 47 is fixed to the upper end portion of the rear member 55 with bolts, or the like, and the fixing plate 47 protrudes rearward from the rear member 55.

A supporting member 70 is provided at the rear end portion of the rod 64 that protrudes rearward from the rear member 55. The supporting member 70 is provided so as to protrude downward. An adjustment tool 71 formed of a bolt is fitted to the supporting member 70. The adjustment tool 71 is screwed to the supporting member 70 so as to extend through the supporting member 70 in the front-rear direction, and the screwed position is fixed by a lock nut 72. The front end of the adjustment tool 71 is in contact with a receiving bolt (receiving member) 73 that is fitted to the rear member 55. The adjustment tool 71 is rotated to be moved in the front-rear direction to adjust the clearance between the front end of the adjustment tool 71 and the receiving bolt 73. Thus, the amount (stroke amount) by which the rod 64 of the second cylinder 56 is movable in the front-rear direction is adjustable.

As shown in FIG. 5, a rear spring receiving portion 75 that protrudes downward is provided at the rear end portion of the device body portion 36, and a front spring receiving portion 76 is provided on the rear surface of the rear member 55 of the sensor supporting portion 38. An urging member (urging device) 77 formed of a compression coil spring is interposed between the front and rear spring receiving portions 75 and 76. The sensor supporting portion 38 is urged forward by the urging member 77. In addition, the urging force of the urging member 77 is adjustable by an adjustment screw 78 provided at the rear spring receiving portion 75.

Next, a flaw detection testing method using the above-described flaw detection testing device 35 will be described. The description will be provided mainly on a method of initially setting the position of the eddy current sensor 37 such that the eddy current sensor 37 is arranged at the predetermined clearance s (see FIG. 4) with respect to the clinched portion 22 of the hub unit 11 that is a test target. Note that, in the following description, the clearance between the clinched portion 22 and the eddy current sensor 37 is set to be within a range from 0.3 to 0.4 mm. In contrast to this, variations in the diameter of the outer peripheral surface of the clinched portion 22 are about 0.5 mm in radius (about 1 mm in diameter).

First, before the position of the eddy current sensor 37 is initially set, the device body portion 36 of the flaw detection testing device 35 is moved rearward and arranged at a position spaced apart from the hub unit 11 in advance. In addition, the sensor supporting portion 38 is moved rearward with respect to the device body portion 36. The rearward movement is performed by maximally extending the gauge head 52 of the micrometer 50 rearward.

Subsequently, the adjustment tool 71 is rotated to set the stroke amount of the rod 64 of the second cylinder 56 at a predetermined value. Here, the stroke amount is set to 1 mm that is slightly larger than 0.3 to 0.4 mm that is the final clearance s between the clinched portion 22 and the eddy current sensor 37. After that, the device body portion 36 is moved forward toward the hub unit 11. At the current stage, neither the eddy current sensor 37 nor the clearance setting member 66 contacts the hub unit 11 just by moving the device body portion 36 forward.

Subsequently, the adjustment knob of the micrometer 50 is operated to contract the gauge head 52 to move the sensor supporting portion 38 forward by the urging force of the urging member 77 to thereby bring the front end of the eddy current sensor 37 into contact with the outer peripheral surface of the clinched portion 22. Then, the adjustment knob of the micrometer 50 is operated in the reverse direction to extend the gauge head 52 to thereby adjust the clearance between the eddy current sensor 37 and the outer peripheral surface of the clinched portion 22 to a value within the range of 0.3 to 0.4 mm.

Subsequently, the second cylinder 56 is actuated so as to move the rod 64 forward. At this time, the stroke amount of the rod 64 is set by the adjustment tool 71 at about 1 mm in advance. Then, the adjustment tool 71 is gradually loosened (relatively moved rearward) to increase the forward stroke amount of the rod 64 to thereby bring the contact portions 67 of the clearance setting member 66 into contact with the outer peripheral surface of the clinched portion 22. Through this operation, the relative position between the clearance setting member 66 and the eddy current sensor 37 with reference to the outer peripheral surface of the clinched portion 22, that is, the clearance s between the outer peripheral surface of the clinched portion 22 and the eddy current sensor 37 at the time when the contact portions 67 of the clearance setting member 66 are brought into contact with the outer peripheral surface of the clinched portion 22, is adjusted. Thus, the adjustment tool 71 constitutes an adjustment device that adjusts the relative position between the clearance setting member 66 and the eddy current sensor 37 with respect to the outer peripheral surface of the clinched portion 22.

Subsequently, the screwed amount of the adjustment screw 78 is adjusted to set the urging force of the urging member 77 at a predetermined value. After that, the gauge head 52 of the micrometer 50 is contracted to separate the distal end of the gauge head 52 from the retaining member 61 by about 2 to 3 mm. Thus, the contact portion 67 of the clearance setting member 66 is pressed against the outer peripheral surface of the clinched portion 22 at a constant urging force. At this stage, the eddy current sensor 37 is positioned by the clearance setting member 66 at a position spaced apart 0.3 to 0.4 mm from the clinched portion 22.

After that, the rod 43 of the first cylinder 44 is moved downward to hold the fixing plate 47 between the stopper member 45 and the stopper receiving portion 46 to thereby restrict movement of the sensor supporting portion 38 in the front-rear direction. The position of the eddy current sensor 37 is fixed through this operation.

Subsequently, the second cylinder 56 is actuated to move the rod 64 rearward to thereby separate the contact portions 67 of the clearance setting member 66 away from the outer peripheral surface of the clinched portion 22. Thus, the second cylinder 56 constitutes an actuating device that moves contact portions 67 of the clearance setting member 66 in the direction in which the contact portions 67 are separated from the outer peripheral surface of the clinched portion 22. Through the above operation, the clearance s between the eddy current sensor 37 and the clinched portion 22 is set at a predetermined value, and the contact portions 67 of the clearance setting member 66 are separated from the clinched portion 22.

After that, the hub unit 11 is rotated for several seconds at a rotation speed of 60 to 100 rpm, and the value detected by the eddy current sensor 37 during this period is read to thereby check whether a flaw or a crack has occurred in the clinched portion 22 of the hub unit 11. The eddy current sensor 37 is arranged at the constant clearance s from the outer peripheral surface of the clinched portion 22, and the contact portions 67 of the clearance setting member 66 are separated from the outer peripheral surface of the clinched portion 22. Therefore, it is possible to prevent occurrence of noise due to contact of the contact portions 67 with the outer peripheral surface of the clinched portion 22, and it is possible to carry out a more accurate flaw detection test. In addition, the contact portions 67 of the clearance setting member 66 are separated from the clinched portion 22. Therefore, it is possible to prevent not only the contact portions 67 from hindering rotation of the hub unit 11 but also a new flaw from occurring in the clinched portion 22.

When a flaw detection test is carried out on a product of the same type subsequently, it is not necessary to newly carry out the above-described initial setting. In a state where the device body portion 36 is moved rearward to be separated from the hub unit 11, fixation of the sensor supporting portion 38 provided by the fixing mechanism 42 (first cylinder 44) is cancelled. Then, the device body portion 36 is moved forward to approach the hub unit 11, and the rod 64 of the second cylinder 56 is moved forward by the stroke amount adjusted by the adjustment tool 71 to thereby return the contact portions 67 of the clearance setting member 66 and the eddy current sensor 37 to a predetermined arrangement state. Thus, the contact portions 67 of the clearance setting member 66 are brought into contact with the outer peripheral surface of the clinched portion 22 by the urging member 77 at a constant urging force, and the clearance s between the outer peripheral surface and the eddy current sensor 37 is also appropriately set. Thus, it is possible to accurately carry out the next and following tests as well, and it is possible to obtain stable test results as a whole.

For the hub unit 11 of a different type having a different diameter of the outer periphery of the clinched portion 22, the above-described initial setting is newly carried out to thereby make it possible to carry out an accurate flaw detection test.

The invention is not limited to the above embodiment; it may be modified in design as appropriate. For example, when movement of the sensor supporting portion 38 in the front-rear direction with respect to the device body portion 36 is fixed, the first cylinder 44 is used to clamp the fixing plate 47 of the sensor supporting portion 38. However, the invention is not limited to this configuration. A stopper (brake), or the like, that restricts forward movement of the sensor supporting portion 38 may be provided. In addition, instead of the second cylinder 56 for moving the clearance setting member 66 in the front-rear direction, an actuator that is able to move linearly, such as a linear actuator, may be used.

In addition, in the above embodiment, a flaw detection test is carried out by the eddy current sensor 37 in a state where the clearance setting member 66 is separated from the outer peripheral surface of the clinched portion 22. Alternatively, a flaw detection test may be carried out in a state where the clearance setting member 66 is in contact with the clinched portion 22. As the flaw detection sensor, not only the eddy current sensor 37 but also any sensor that is able to detect a flaw or a crack with a clearance from the outer peripheral surface of the clinched portion 22 may be employed. The flaw detection testing device according to the invention may be applied to the configuration where no spline teeth are formed at the clinched portion of the hub unit.

According to the invention, it is possible to carry out an accurate flaw detection test without adjusting the clearance between the outer peripheral surface of the clinched portion and the flaw detection sensor for each product for the plurality of hub units.

What is claimed is:

1. A flaw detection testing device that carries out a flaw detection test on an outer peripheral surface of a clinched portion used to fix an inner ring member of a hub unit to a hub spindle, comprising:
    a flaw detection sensor;
    a clearance setting member that contacts the outer peripheral surface of the clinched portion to set a clearance between the flaw detection sensor and the outer peripheral surface of the clinched portion at a predetermined value; and
    a fixing device that fixes a position of the flaw detection sensor with the clearance between the flaw detection sensor and the outer peripheral surface of the clinched portion kept at the predetermined value; and
    an actuating device that moves the clearance setting member in such a direction that the clearance setting member is separated from the outer peripheral surface of the clinched portion with the position of the flaw detection sensor fixed by the fixing device.

2. The flaw detection testing device according to claim 1, further comprising:
    an adjustment device that adjusts a relative position between the clearance setting member and the flaw detection sensor with reference to the outer peripheral surface of the clinched portion.

3. The flaw detection testing device according to claim 1, further comprising:
    an urging device that applies a predetermined contact pressure to the clearance setting member when the clearance setting member is brought into contact with the outer peripheral surface of the clinched portion.

4. The flaw detection testing device according to claim 1, wherein
    the clearance setting member has at least two contact portions, and
    the two contact portions contact the outer peripheral surface of the clinched portion at two portions that are apart from each other in a circumferential direction with the flaw detection sensor interposed between the two contact portions.

5. A flaw detection testing device that carries out a flaw detection test on an outer peripheral surface of a clinched portion used to fix an inner ring member of a hub unit to a hub spindle, comprising:

a flaw detection sensor;

a sensor supporting portion that supports the flaw detection sensor, and that is movable in such a direction that the flaw detection sensor is brought close to the outer peripheral surface of the clinched portion and in a such direction that the flaw detection sensor is separated from the outer peripheral surface of the clinched portion;

a clearance setting member that is provided for the sensor supporting portion and that, when the flaw detection sensor is brought close to the outer peripheral surface of the clinched portion, contacts the outer peripheral surface to thereby set a clearance between the outer peripheral surface and the flaw detection sensor at a predetermined value;

a fixing device that fixes a position of the sensor supporting portion with the clearance between the flaw detection sensor and the outer peripheral surface of the clinched portion kept at the predetermined value; and an actuating device that moves the clearance setting member in such a direction that the clearance setting member is separated from the outer peripheral surface of the clinched portion with the position of the sensor supporting portion fixed by the fixing device.

6. The flaw detection testing device according to claim 5, further comprising:

an urging device that applies a predetermined contact pressure to the clearance setting member when the clearance setting member is brought into contact with the outer peripheral surface of the clinched portion.

7. The flaw detection testing device according to claim 5, wherein the clearance setting member has at least two contact portions, and the two contact portions contact the outer peripheral surface of the clinched portion at two portions that are apart from each other in a circumferential direction with the flaw detection sensor interposed between the two contact portions.

8. The flaw detection testing device according to claim 5, further comprising:

an adjustment device that adjusts a relative position between the clearance setting member and the flaw detection sensor with reference to the outer peripheral surface of the clinched portion.

9. The flaw detection testing device according to claim 8, further comprising:

an urging device that applies a predetermined contact pressure to the clearance setting member when the clearance setting member is brought into contact with the outer peripheral surface of the clinched portion.

10. The flaw detection testing device according to claim 8, wherein the clearance setting member has at least two contact portions, and the two contact portions contact the outer peripheral surface of the clinched portion at two portions that are apart from each other in a circumferential direction with the flaw detection sensor interposed between the two contact portions.

11. A flaw detection testing device that carries out a flaw detection test on an outer peripheral surface of a clinched portion used to fix an inner ring member of a hub unit to a hub spindle, comprising:

a flaw detection sensor;

a clearance setting member that contacts the outer peripheral surface of the clinched portion to set a clearance between the flaw detection sensor and the outer peripheral surface of the clinched portion at a predetermined value;

a fixing device that fixes a position of the flaw detection sensor with the clearance between the flaw detection sensor and the outer peripheral surface of the clinched portion kept at the predetermined value; and an adjustment device that adjusts a relative position between the clearance setting member and the flaw detection sensor with reference to the outer peripheral surface of the clinched portion.

12. A flaw detection testing device that carries out a flaw detection test on an outer peripheral surface of a clinched portion used to fix an inner ring member of a hub unit to a hub spindle, comprising:

a flaw detection sensor;

a clearance setting member that contacts the outer peripheral surface of the clinched portion to set a clearance between the flaw detection sensor and the outer peripheral surface of the clinched portion at a predetermined value;

a fixing device that fixes a position of the flaw detection sensor with the clearance between the flaw detection sensor and the outer peripheral surface of the clinched portion kept at the predetermined value; and an urging device that applies a predetermined contact pressure to the clearance setting member when the clearance setting member is brought into contact with the outer peripheral surface of the clinched portion.

* * * * *